(12) United States Patent
Pracar et al.

(10) Patent No.: US 9,924,900 B2
(45) Date of Patent: Mar. 27, 2018

(54) MONITORING, TRACKING, AND MANAGING SYMPTOMS OF AUTISM SPECTRUM DISORDER

(71) Applicants: Alexis Pracar, Piedmont, CA (US);
Shane Pracar, Piedmont, CA (US)

(72) Inventors: Alexis Pracar, Piedmont, CA (US);
Shane Pracar, Piedmont, CA (US)

( * ) Notice: Subject to any disclaimer, the term of this patent is extended or adjusted under 35 U.S.C. 154(b) by 0 days.

(21) Appl. No.: 14/021,449

(22) Filed: Sep. 9, 2013

(65) Prior Publication Data

US 2015/0073309 A1 Mar. 12, 2015

(51) Int. Cl.
*A61B 5/00* (2006.01)
*A61B 5/11* (2006.01)
*A61M 21/00* (2006.01)

(52) U.S. Cl.
CPC ............ *A61B 5/4836* (2013.01); *A61B 5/11* (2013.01); *A61B 5/4094* (2013.01); *A61B 5/681* (2013.01); *A61B 5/74* (2013.01); *A61M 21/00* (2013.01); *A61B 5/0002* (2013.01); *A61B 5/486* (2013.01); *A61B 5/7455* (2013.01); *A61M 2021/005* (2013.01); *A61M 2021/0022* (2013.01); *A61M 2021/0027* (2013.01); *A61M 2205/332* (2013.01); *A61M 2205/3569* (2013.01); *A61M 2205/3592* (2013.01); *A61M 2205/505* (2013.01); *A61M 2205/52* (2013.01); *A61M 2205/582* (2013.01); *A61M 2205/583* (2013.01); *A61M 2205/8206* (2013.01); *A61M 2209/088* (2013.01); *A61M 2230/63* (2013.01)

(58) Field of Classification Search
CPC ..... A61M 21/02; A61B 5/1118; A61B 5/4836
See application file for complete search history.

(56) References Cited

U.S. PATENT DOCUMENTS

2007/0085690 A1* 4/2007 Tran ................. A61B 5/103
340/573.1
2011/0004072 A1* 1/2011 Fletcher .............. A61B 5/0002
600/300

(Continued)

OTHER PUBLICATIONS

"Autism", Wikipedia, [Online]. Retrieved from the Internet: < http://en.wikipedia.org/wiki/Autism >, Accessed on Aug. 1, 2013, 20 pgs.

(Continued)

*Primary Examiner* — Daniel Cerioni
*Assistant Examiner* — Yasmeen S Warsi
(74) *Attorney, Agent, or Firm* — Kwan & Olynick LLP

(57) ABSTRACT

Various embodiments of the present invention describe mechanisms configured to monitor, track, and manage symptoms of autism spectrum disorder. According to particular embodiments, a system includes sensors configured to monitor repetitive motion exhibited by a user with an autism spectrum disorder (ASD). The sensors are connected to a processor that is configured to determine whether the repetitive motion exhibited by the user exceeds an autism episode threshold. Once the autism episode threshold has been reached, the processor can access from memory an autism episode alleviation action associated with the user. Materials associated with the autism episode alleviation action can be presented to the user through an output interface, such that presentation of these materials is configured to reduce the severity or duration of the autism episode.

18 Claims, 5 Drawing Sheets

(56) References Cited

U.S. PATENT DOCUMENTS

2011/0199205 A1* 8/2011 Kreml ................... A61B 5/1118
340/539.11
2011/0245633 A1* 10/2011 Goldberg ............... A61B 5/681
600/301

OTHER PUBLICATIONS

"Symptons: What are the Symptons of Autism?", [Online]. Retrieved from the Internet: < http://www.autismspeaks.org/what-autism/symptoms >, Accessed on Aug. 1, 2013, 4 pgs.

Rudy, Lisa J. , "All About Sensory Integration Therapy and Autism", [Online]. Retrieved from the Internet: < http://autism.about.com/od/treatmentoptions/a/allaboutsi.htm?p=1 >, Accessed on Aug. 1, 2013, 2013, 1 pg.

Rudy, Lisa J. , "Repetitive Behaviors in Autism", [Online]. Retrieved from the Internet: < http://autism.about.com/od/whatisautism/a/perseveration.htm >, Accessed on Aug. 1, 2013, 2013, 2 pgs.

Rudy, Lisa J. , "The "Floortime" Treatment for Autism", [Online]Retrieved from the Internet: <http://autism.about.com/od/developmentaltreatments/a/floortimeplay.htm> Accessed on Aug. 1, 2013, 2013, 1 pg.

* cited by examiner

MONITORING, TRACKING, AND MANAGING SYMPTOMS OF AUTISM SPECTRUM DISORDER

TECHNICAL FIELD

The present disclosure relates to monitoring, tracking, and managing symptoms of autism spectrum disorder.

DESCRIPTION OF RELATED ART

Autism spectrum disorder (ASD) is a neurodevelopmental disorder that is characterized by impairments in social interaction and communication, restricted interests, and repetitive behavior. The degree and type of impairment in each of these areas can vary widely between individuals, with some facing mild impairments and others facing severe impairments. ASD usually presents life-long challenges and both children and adults affected by the disorder can benefit greatly from interventions and therapies that can reduce symptoms and increase skills and abilities.

Symptoms of ASD usually begin to appear in young children before the age of three. Although early detection and interventions are encouraged to maximize the benefits and reduce the severity of the symptoms, individuals of any age can benefit from interventions and therapies.

Stress, anxiety, and upset can cause individuals to express repetitive behaviors (also known as perseveration). Common stressors include unfamiliar, overwhelming or frustrating situations. Some examples of repetitive behaviors include hand flapping, head rolling, or body rocking. Other examples include stacking or lining up objects. Individuals may also have difficulty regulating emotions and can have outbursts at inappropriate times and in inappropriate settings. In some cases, frustrations and stressors can also involve self-injurious behaviors such as head banging, self-biting, skin picking, eye poking, and hair pulling.

Various theories exist regarding the causes and appropriate therapies for repetitive behaviors in individuals with ASDs. One theory is that repetitive behaviors are a behavior issue that can be addressed by behavioral therapy. Another theory is that repetitive behaviors are a calming mechanism to block out overwhelming sensory input. According to this theory, sensory integration techniques can be used to regulate the behaviors. Another theory is that the repetitive behaviors involve and reflect the true interests of the person with ASD. In such cases, therapeutic techniques for play can help the individual turn the repetitive behaviors into meaningful play. Yet another theory posits that anxiety and/or a neural or chemical issue that causes the repetitive behavior can be addressed with pharmacotherapy.

Each of the theories set forth involve therapies that can be expensive and time-intensive. Furthermore, these therapies may be available only at specific times, such as at weekly therapy sessions. Accordingly, it is desirable to provide improved mechanisms to address repetitive behaviors in individuals with ASD.

SUMMARY

Various embodiments of the present invention describe mechanisms configured to monitor, track, and manage symptoms of autism spectrum disorder. According to particular embodiments, a system includes sensors configured to monitor repetitive motion exhibited by a user with an autism spectrum disorder (ASD). The sensors are connected to a processor that is configured to determine whether the repetitive motion exhibited by the user exceeds an autism episode threshold. Once the autism episode threshold has been reached, the processor can access from memory an autism episode alleviation action associated with the user. Materials associated with the autism episode alleviation action can be presented to the user through an output interface, such that presentation of these materials is configured to reduce the severity or duration of the autism episode.

BRIEF DESCRIPTION OF THE DRAWINGS

The disclosure may best be understood by reference to the following description taken in conjunction with the accompanying drawings, which illustrate particular embodiments of the present invention.

DETAILED DESCRIPTION

Figure 1:
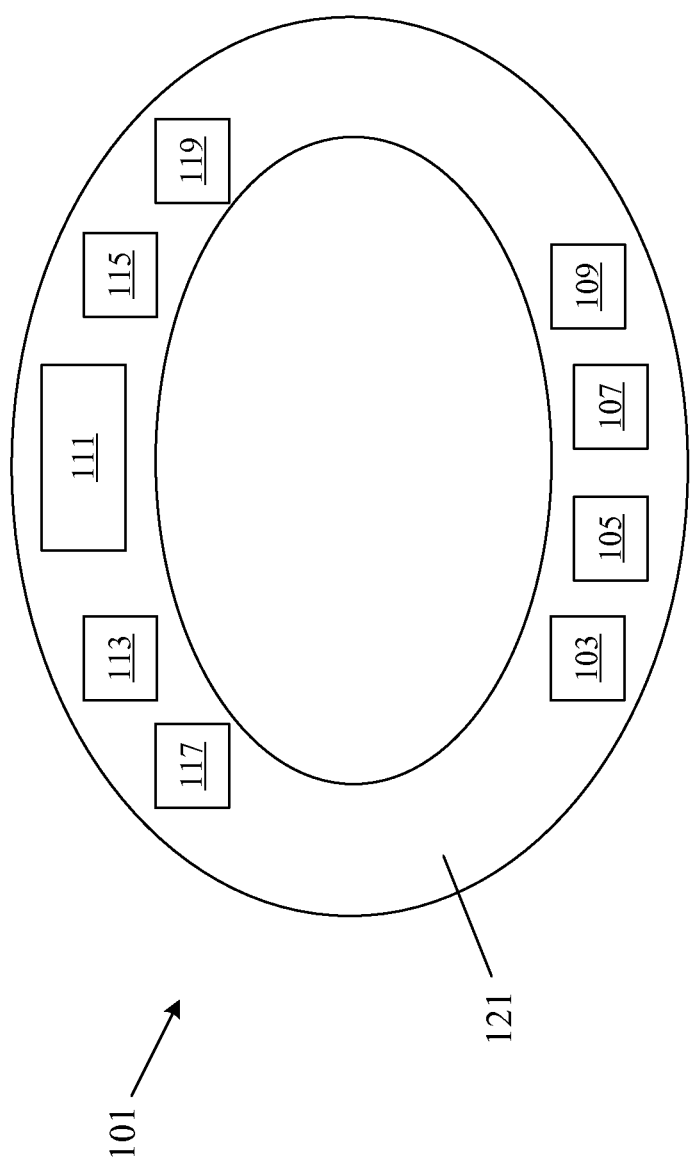
FIG. 1 illustrates one example of a system configured to monitor repetitive motion of a user on the autism spectrum.

Reference will now be made in detail to some specific examples of the invention including the best modes contemplated by the inventors for carrying out the invention. Examples of these specific embodiments are illustrated in the accompanying drawings. While the invention is described in conjunction with these specific embodiments, it will be understood that it is not intended to limit the invention to the described embodiments. On the contrary, it is intended to cover alternatives, modifications, and equivalents as may be included within the spirit and scope of the invention as defined by the appended claims.

In the following description, numerous specific details are set forth in order to provide a thorough understanding of the present invention. Particular example embodiments of the present invention may be implemented without some or all of these specific details. In other instances, well known process operations have not been described in detail in order not to unnecessarily obscure the present invention.

Autism spectrum disorder (ASD) is a neurodevelopmental disorder that is characterized by impairments in social interaction and communication, restricted interests, and repetitive behavior. Individuals on the autism spectrum experience widely varying degrees and types of impairments, from mild to severe. Symptoms of ASD usually begin to appear in young children before the age of three and ASD usually presents life-long challenges. Although early detection and interventions are encouraged to maximize the benefits and reduce the severity of the symptoms, individuals of any age can benefit from interventions and therapies that can reduce symptoms and increase skills and abilities.

One common symptom of ASD is repetitive behavior (also known as perseveration). Stress, anxiety, and upset can cause individuals to express various repetitive behaviors. Common stressors include unfamiliar, overwhelming or frustrating situations. Some examples of repetitive behaviors include hand flapping, head rolling, or body rocking. Other examples include stacking or lining up objects.

Individuals with ASD may also have difficulty regulating emotions and can have outbursts at inappropriate times and in inappropriate settings. In some cases, frustrations and stressors can lead to not only repetitive behavior, but also self-injurious behavior. Examples of self-injurious behaviors include head banging, self-biting, skin picking, eye poking, and hair pulling. Some of these self-injurious behaviors can also be repetitive in nature.

Current treatments and therapies for repetitive behaviors associated with ASD vary. Because there are different theories regarding the causes of such repetitive behaviors, the associated therapies also differ depending on which theory seems applicable. If the repetitive behavior is considered a behavior issue, it can be addressed by behavioral therapy. If the repetitive behavior is seen as a calming mechanism to block out overwhelming sensory input, sensory integration techniques can be therapeutic. If the repetitive behavior involves and reflects the true interests of the person with ASD, therapeutic techniques for play can help turn the repetitive behaviors into meaningful play. If anxiety and/or a neural or chemical issue are believed to cause the repetitive behavior, pharmacotherapy may be an appropriate therapy.

Each of the theories described above typically involve therapies that can be expensive and time-intensive. Furthermore, these therapies may be available only at specific times, such as at weekly therapy sessions. Although these sessions can be useful in overall treatment, they do not address individual ASD episodes or repetitive behaviors in real-time. Consequently, individuals with ASD and their families and/or caregivers may be left to deal with individual episodes or outbursts most of the time. Consequently, it is desirable to provide improved mechanisms to address ASD symptoms when they occur.

Consequently, the techniques and mechanisms of the present invention provide therapy alternatives that can address specific ASD episodes of repetitive behavior when they occur. This provides advantages over traditional therapies that commonly involve weekly therapy sessions. According to various embodiments of the present invention, sensors are configured to monitor repetitive motion exhibited by a user with an autism spectrum disorder (ASD). If the repetitive motion reaches a sufficient threshold, an autism episode alleviation action can be presented to the user. In particular embodiments, tracking and monitoring repetitive motion can provide perspective about whether specific therapies or autism alleviation actions are effective, and whether ASD episodes or repetitive behaviors are improving or worsening over time.

FIG. 1 illustrates one example of a system configured to monitor repetitive motion of a user on the autism spectrum. As shown, the system 101 includes a band 121 with a memory 103, processor 105, and sensors 107. The sensors 107 can include one or more devices such as a gyroscope, accelerometer, gravimeter, and/or the like. The sensors 107 can be selected and configured to measure and detect repetitive motion associated with an autism episode (i.e. repetitive behavior). Processor 105 can be configured to compare the detected repetitive motion to an autism episode threshold and determine whether the user is experiencing an autism episode. Memory 103 can hold an autism episode alleviation action associated with the user. The autism episode alleviation action can be selected to reduce the severity or duration of the autism episode. This autism episode alleviation action can be accessed by processor 105 once an autism episode threshold has been reached.

In some exemplary embodiments, the system can include a network interface 109, which can include a plug, USB connection, Bluetooth, or the like. This network interface can allow the system to communicate and/or exchange data with other devices such as a smart phone, computer, etc. However, it should be noted that the system can be constructed to operate independently without a network interface in some embodiments.

In the present exemplary embodiment, the system can include an output interface 111, such as a touch screen or display. Some examples of displays that can be used with the present invention include a liquid crystal display (LCD), a flexible organic light emitting diode (OLED) display, a magnetic display, and a microelectromechanical systems (MEMS) display. The output interface 111 can present materials from an autism episode alleviation action to the user once an autism episode has been detected by the system 101. The autism episode alleviation action can be selected to reduce the severity or duration of the autism episode. For instance, the autism episode alleviation action can include video, pictures, color displays, games, and the like, that can be displayed on the output interface 111. In some embodiments, the output interface 111 can also receive input, such as when a touch screen is used.

According to various exemplary embodiments, the band 121 can include a speaker 113. The speaker 113 can present materials from an autism episode alleviation action to the user once an autism episode has been detected by the system. In some examples, the autism episode alleviation action can include a song, recording, voice message, or other audio track that can be played for the user. The autism episode alleviation action can be selected to reduce the severity or duration of the autism episode.

Optionally, the band 101 can include a notification light 115. In some exemplary embodiments, this notification light can turn on, flash and/or blink when an autism episode is detected. Alternatively, this notification light can be used to display system conditions such as battery life, etc. This notification light may be a single color or multiple colors. In particular, the light could display a different color for different types of notifications, such as battery status, sleep mode, awake mode, etc. In other embodiments, the light could take the form of different shapes displayed for different types of notifications. For instance, awake mode could display a light in the shape of an open eye, sleep mode could display a light in the shape of a closed eye, and battery life can display a light in the shape of a battery, etc. The color of the shaped light might indicate whether the battery is fully charged (e.g. green), partially charged (e.g. yellow), or needs charge (e.g. red).

According to various exemplary embodiments, band 121 can optionally include a vibration mechanism 117. The vibration mechanism 117 can be used in various ways. For instance, vibrations can be used to alert the user about a repetitive motion. In another example, vibrations can be used in conjunction with an alarm or reminder. For instance, the user could set an alarm to take walking breaks every hour and the band 121 would vibrate according to this schedule. In yet other examples, the vibrations could provide therapeutic sensations for the user and can be incorporated with an autism episode alleviation action.

In some exemplary embodiments, the band 121 can include one or more buttons 119. These buttons can be used to control the output interface 111, speaker 113, notification light 115, vibration mechanism 117, or other parts of the system 101. For instance, it can be used to make a selection presented by the output interface 111, adjust the volume of the speaker 113, and/or activate the notification light 115.

According to the present embodiment, the band 121 can be designed as a bracelet, wristband, or other wearable device. Band 121 can be constructed from various materials, such as elastic, plastic, vinyl, rubber, etc. The material of the band can be rigid (like a hard plastic, etc.) or flexible (like silicone, rubber, etc.). According to various embodiments, the band 121 can be adjustable in size. For instance, band 101 can include a buckle, latch, or the like. In other examples, band 121 can overlap itself like a slap bracelet, so that it can be sized the user more easily. In another example, the band 121 can form a U-shape that can either leave an opening on one portion of the length or overlap itself to some extent. In yet other examples, band 121 can have a clasp that can adjustably attach to links, loops, or other openings on the band 121.

It should be noted that although the present embodiment shows a certain configuration of the components in band 121, the configuration is illustrative only and does not intend to limit the placement of various components. For instance, the location of speaker 113 and buttons 119 can be exchanged. Similarly, other components of the system 101 can be moved with respect to one another without departing from the scope of the present invention.

Figure 2:
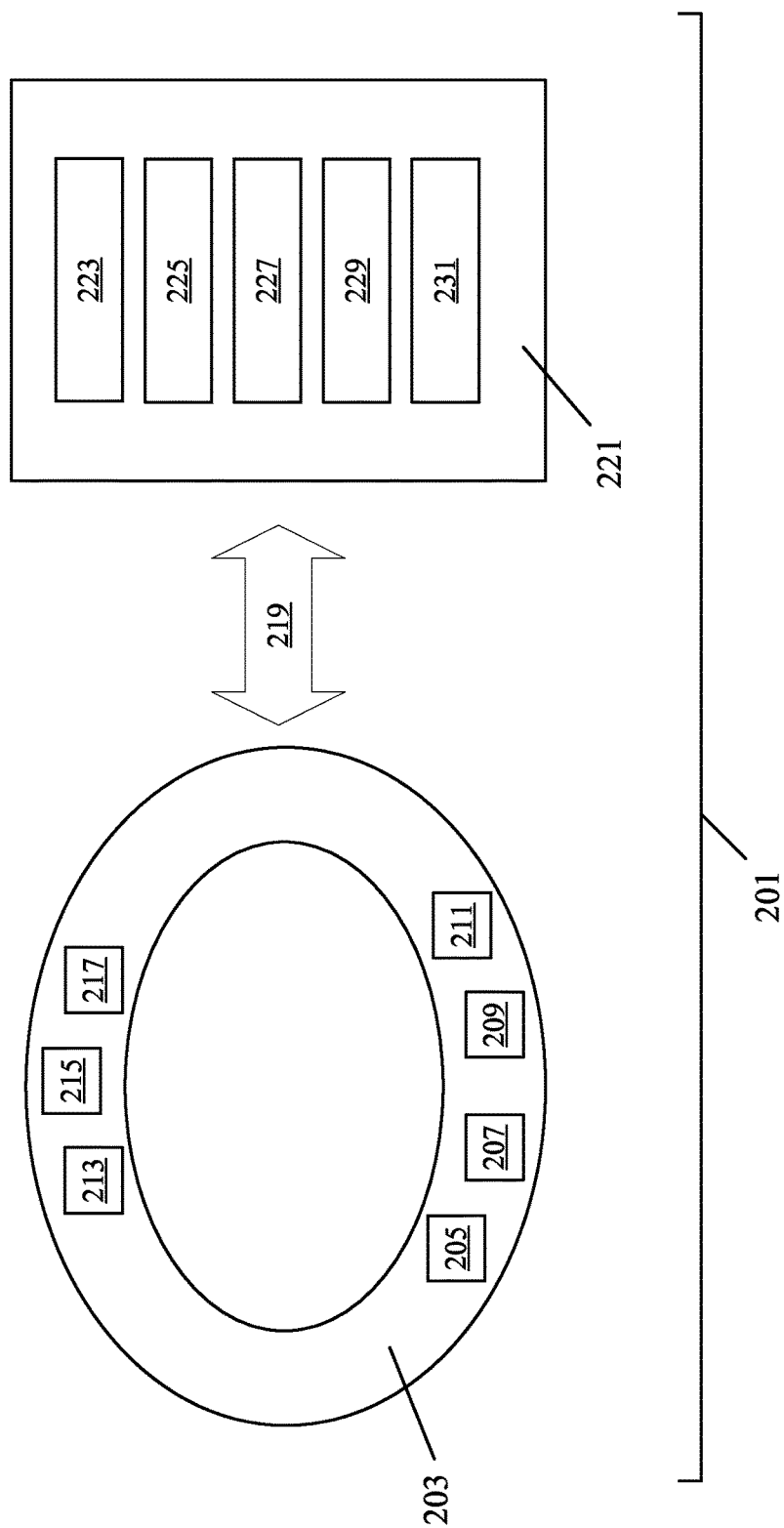
FIG. 2 illustrates another example of a system configured to monitor repetitive motion of a user on the autism spectrum.

FIG. 2 illustrates another example of a system configured to monitor repetitive motion of a user on the autism spectrum. As shown, the system 201 includes a band 203 and remote device 221. According to the present embodiment, the band 203 can be designed as a bracelet, wristband, or other wearable device. Furthermore, remote device 221 can be a smart phone, computer, laptop, tablet, notebook, portable gaming device, or other interactive device.

In the present exemplary embodiment, band 203 includes sensors 205. The sensors 205 can include one or more devices such as a gyroscope, accelerometer, gravimeter, and/or the like. The sensors 205 can be selected and configured to measure and detect repetitive motion associated with an autism episode (i.e. repetitive behavior).

Optionally, the band 203 can include a notification light 213. In some exemplary embodiments, this notification light 213 can turn on, flash and/or blink when an autism episode is detected. Alternatively, this notification light can be used to display system conditions such as battery life, etc. This notification light 213 may display a single color or multiple colors. In particular, the light could display a different color for different types of notifications, such as battery status, sleep mode, awake mode, etc. In other embodiments, the light could take the form of different shapes displayed for different types of notifications. For instance, awake mode could display a light in the shape of an open eye, sleep mode could display a light in the shape of a closed eye, and battery life can display a light in the shape of a battery, etc. The color of the shaped light might indicate whether the battery is fully charged (e.g. green), partially charged (e.g. yellow), or needs charge (e.g. red).

According to various exemplary embodiments, band 203 can optionally include a vibration mechanism 215. The vibration mechanism 215 can be used in various ways. For instance, vibrations can be used to alert the user about a repetitive motion. In another example, vibrations can be used in conjunction with an alarm or reminder. For instance, the user could set an alarm to take walking breaks every hour and the band 203 would vibrate according to this schedule. In yet other examples, the vibrations could provide therapeutic sensations for the user and can be incorporated with an autism episode alleviation action.

In some exemplary embodiments, the band 203 can include one or more buttons 217. These buttons can be used to control notification light 213, interact with a remote device 221, or communicate with other parts of the band 203. For instance, it can be used to activate the notification light 213, such as to determine the current mode (e.g. awake, asleep, etc.) or to activate or switch to a certain mode (e.g. change from awake to asleep).

According to various exemplary embodiments, band 203 can be constructed from various materials, such as elastic, plastic, vinyl, rubber, etc. The material of the band can be rigid (like a hard plastic, etc.) or flexible (like silicone, rubber, etc.). According to various embodiments, the band 203 can be adjustable in size. For instance, band 203 can include a buckle, latch, or the like. In other examples, band 203 can overlap itself like a slap bracelet, so that it can be sized the user more easily. In another example, the band 203 can form a U-shape that can either leave an opening on one portion of the length or overlap itself to some extent. In yet other examples, band 203 can have a clasp that can adjustably attach to links, loops, or other openings on the band 203.

According to various exemplary embodiments, band 203 can optionally include simple memory 207 and/or simple processor 209. In some examples, simple memory 207 and/or simple processor 209 can be used to detect input from buttons 217. Additionally, simple memory 207 and/or simple processor 209 can be used to control notification light 213.

According to the present embodiment, band 203 includes a network interface 211, which can include a plug, USB connection, Bluetooth, or the like. This network interface 211 can allow the band 203 to communicate and/or exchange data with a remote device 221 such as a smart phone, computer, etc. Such communication can occur over a data connection 219 that can be wired, wireless, etc. depending on the chosen communication protocol.

In the present exemplary embodiment, remote device 221 includes an output interface 223, processor 225, memory 227, and speaker 229. Remote device 215 can be can be a smart phone, computer, laptop, tablet, notebook, portable gaming device, or other interactive device. In addition, remote device 221 can exchange, receive, and/or send communications and/or data with band 203 over data connection 219 using network interface 231.

In the present exemplary embodiment, processor 225 can be configured to compare the repetitive motion detected by sensors 205 to an autism episode threshold and determine whether the user is experiencing an autism episode. Furthermore, in the present embodiment, memory 227 can store an autism episode alleviation action associated with the user. The autism episode alleviation action can be selected to reduce the severity or duration of the autism episode. This autism episode alleviation action can be accessed by processor 225 once an autism episode threshold has been reached.

According to the present embodiment, remote device 221 can include an output interface 223, such as a touch screen or display. Some examples of displays that can be used with the present invention include a liquid crystal display (LCD), flexible organic light emitting diode (OLED) display, magnetic display, or microelectromechanical systems (MEMS) display. The output interface 223 can present materials from an autism episode alleviation action to the user once an autism episode has been detected by the sensors 205. The autism episode alleviation action can be selected to reduce the severity or duration of the autism episode. For instance, the autism episode alleviation action can include video, pictures, color displays, games, etc. that can be displayed on the output interface 223. In some embodiments, the output interface 223 can also receive input, such as when a touch screen is used.

In the present embodiment, remote device 221 includes speaker 229. The speaker 229 can present materials from an autism episode alleviation action to the user once an autism episode has been detected by sensors 205. In some examples, the autism episode alleviation action can include a song, recording, voice message, or other audio track that can be played for the user. The autism episode alleviation action can be selected to reduce the severity or duration of the autism episode.

It should be noted that although the present embodiment shows a certain configuration of the components in band 203 and remote device 221 of system 201, the configuration is illustrative only and does not intend to limit the placement of various components. For instance, the location of sensors 205 and vibration mechanism 215 can be exchanged within band 203. Furthermore, the placement of output interface 223 can be exchanged with speaker 229 within remote device 221. Similarly, other components of the system 201 can be moved with respect to one another without departing from the scope of the present invention.

Figure 3:
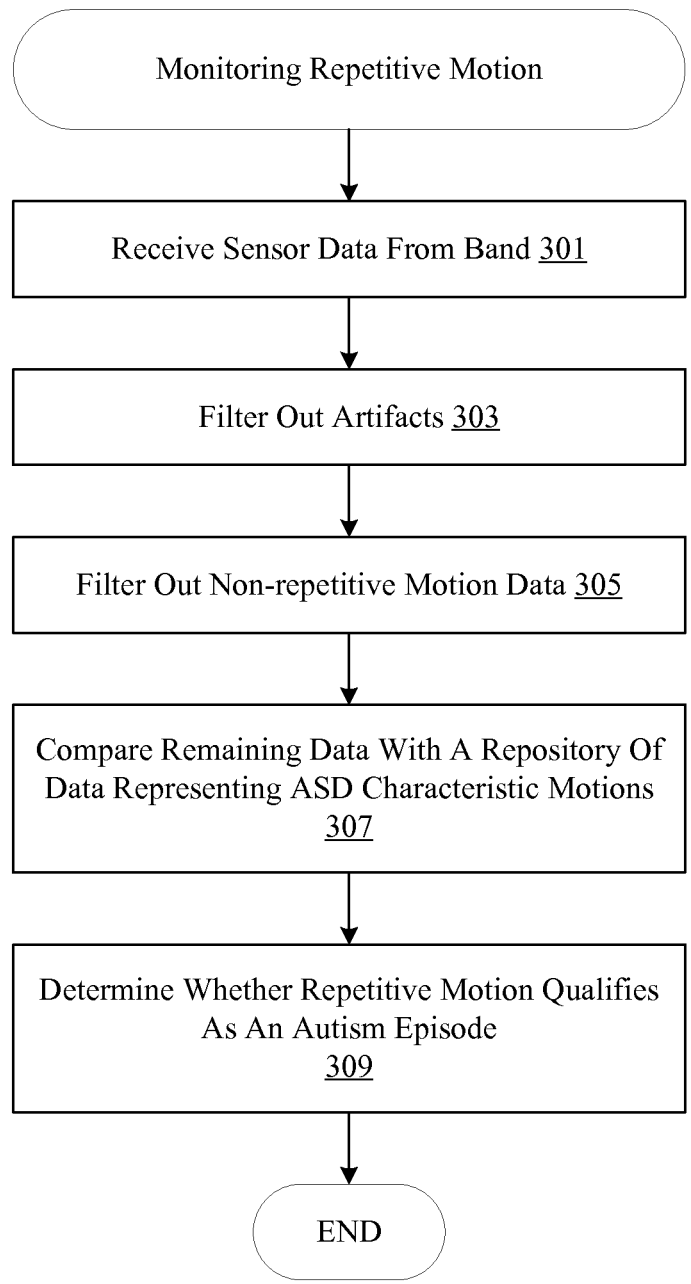
FIG. 3 illustrates an example of monitoring repetitive motion of a user on the autism spectrum.

FIG. 3 illustrates an example of monitoring repetitive motion of a user with an autism spectrum disorder (ASD). Specifically, a user wears a band such as one described with regard to FIGS. 1 and 2 above. Sensors included in the band then detect the user's movements. At 301, sensor data regarding the user's movement is received from the band. According to various exemplary embodiments, the sensor data can be sent in a continuous stream or as packets of information at particular intervals of time. At 303, artifacts are filtered out from the data. Such artifacts can include data representing heartbeats, breathing, chewing, etc. that do not represent repetitive motion associated with an autism episode. Next, at 305, non-repetitive motions are filtered out from the sensor data. Some examples of non-repetitive motions can include moving an arm to grab something, getting up from a chair, sitting down, etc.

The remaining sensor data is then compared with repository data corresponding to ASD characteristic repetitive motions at 307. The repository data can be stored in a database and can include characteristic waveforms corresponding to ASD repetitive movements. The waveforms and/or other repository data can be obtained from medical sources, empirical data, the user's own historical data, etc. In some exemplary embodiments, the repository data could be refined on an ongoing basis using data collected from the user. For instance, each time the system confirms that the user has had an autism episode, waveforms and/or other information gathered during the autism episode could be stored in the database. In the present exemplary embodiment, the repository data can include information corresponding to ASD repetitive motions such as hand flapping, rocking back and forth, spinning, humming, screaming, head rolling, etc. In some embodiments, the repository data can also include information corresponding to ASD self-injurious behaviors that have a repetitive nature such as skin picking, head banging, eye poking, hair pulling, etc.

Once the remaining sensor data is then compared with repository data corresponding to ASD characteristic repetitive motions, a determination is made at 309 whether the remaining sensor data qualifies as an autism episode. For example, a detected repetitive motion can be compared to characteristic data for hand flapping. If the repetitive motion matches or exceeds this characteristic data, then the system determines that the repetitive motion qualifies as an autism episode. In contrast, if the repetitive motion does not match or exceed the characteristic data, then the system determines that the repetitive motion does not qualify as an autism episode. Similarly, the repetitive motion can be compared to the repository data for various types of ASD characteristic repetitive motions to determine if the repetitive motion detected exceeds a threshold determined to qualify as an autism episode. In some embodiments, data about the detected autism episode can be stored for reference. In addition, such data can be added to the database to be used for future detection of autism episodes in some embodiments. Once an autism episode is detected, then the user can be presented with an autism episode alleviation action, as described in more detail below with regard to FIG. 4.

Figure 4:
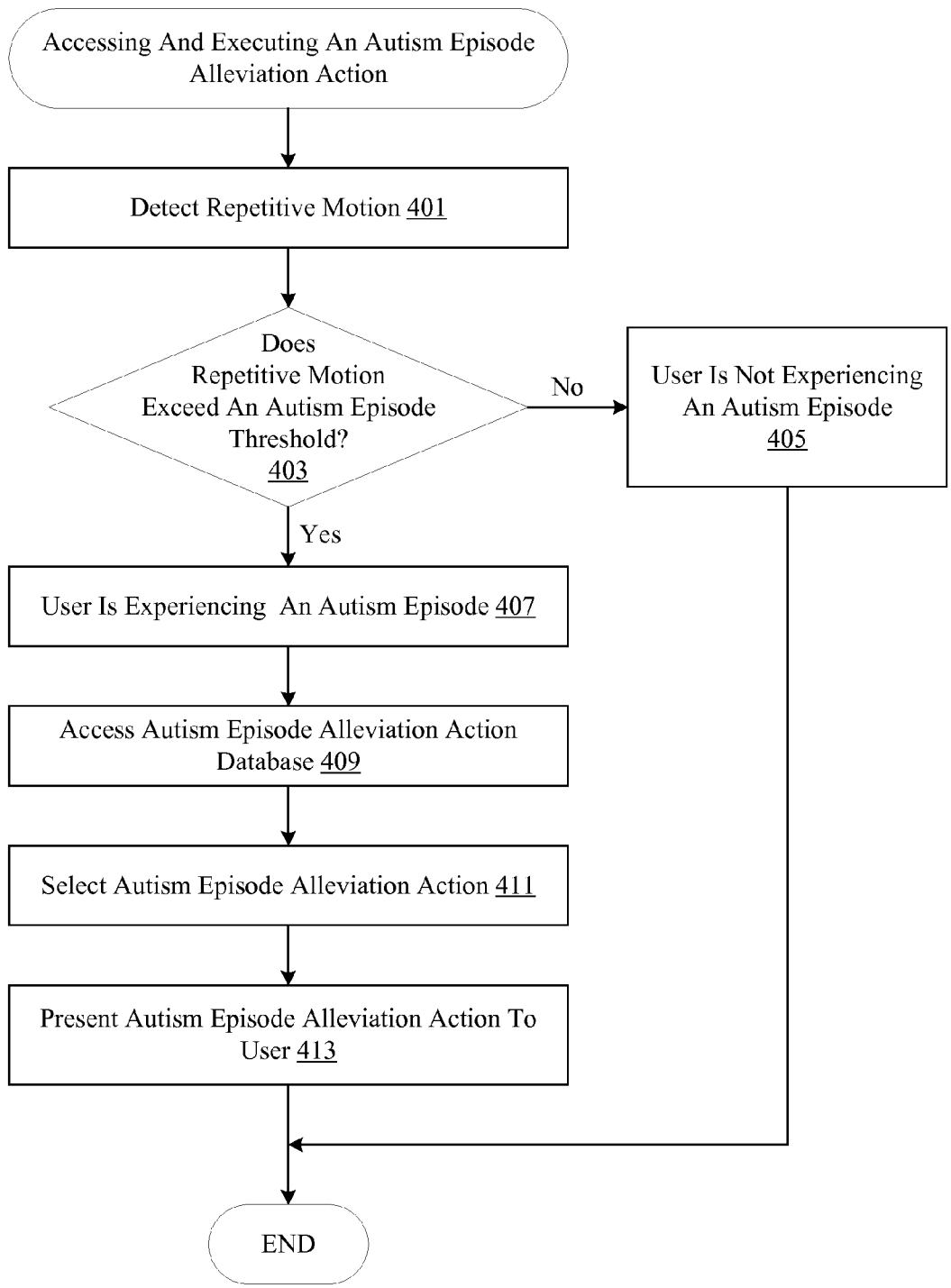
FIG. 4 illustrates an example of accessing and executing an autism episode alleviation action.

FIG. 4 illustrates an example of accessing and executing an autism episode alleviation action. According to this embodiment, the system detects a repetitive motion at 401. As described above with respect to FIG. 3, the repetitive motion data can be sensor data that has been filtered so that artifacts and non-repetitive movements are eliminated. Next, a determination is made whether the repetitive motion exceeds an autism episode threshold at 403. As also described with regard to FIG. 3, the repetitive motion can be compared to repository data corresponding to ASD characteristic repetitive motions. The repository data can delineate the parameters of ASD characteristic motions such that repetitive motions matching or exceeding these parameters qualifies as an autism episode. If the system determines that the user is not experiencing an autism episode at 405, then no further action is taken.

If the system determines that the user is experiencing an autism episode at 407, then an autism episode alleviation action database is accessed at 409. This database can store information about possible actions that can be taken to address an autism episode. For instance, one type of autism alleviation action could be to advise the user to take an action such as breathing deeply or counting to get to a calmer place. In some examples, this advice can be provided via verbal prompts, a verbally-led meditation, or verbal counting. In other examples, an autism alleviation action can prompt the user to push a button to hear a soothing recording or view a video or image. Examples of soothing recordings can include a favorite story, song, poem, dialogue, fun facts about an area of interest, etc. If the user is a child, the recording could also include the mother's voice in some embodiments. Examples of videos can include movie or television clips, calming scenery, slideshows, pictures, etc. In some embodiments, the recording and/or video can continue to repeat and each time the recording and/or video plays it can play at a decreasing volume until at some point the user can transition into another activity. In yet other embodiments, the autism alleviation action can include notifying the user of the repetitive behavior detected. In some examples, this could include providing vibrations through the band and/or audible tones to make the user aware of the behavior. Another example of an autism alleviation action is presenting a game or other interactive experience that can engage or distract the user from the repetitive motion. Yet another example of an autism alleviation action is to provide noise cancelling technology, such as through a remote device or as a prompt to put on noise cancelling headphones or ear plugs. According to various embodiments, one or more autism alleviation actions can be set as preferences by or specifically for the user, so that the user's favorite songs, games, etc. can be specified. Furthermore, a user can set preferences for a customized audio and/or video clip.

Once the autism episode alleviation action database is accessed, an autism episode alleviation action can be selected at 411. In some embodiments a default autism episode alleviation action can be selected once an autism episode is detected. In other embodiments, an autism alleviation action can be selected based on the type of autism episode detected. For example, if the type of autism episode detected is hand flapping, a game could be selected to engage the user both as a mental distraction and as a physical disruption to the repetitive motion. In the present example, if the type of autism episode detected is head rolling, a video could be selected such that the user's attention can be directed towards viewing the video in a manner that would physically disrupt the repetitive head rolling. The selection of the autism episode alleviation action could be based on default settings or could be based on user preferences. Specifically, default settings could specify autism episode alleviation actions that correspond to particular types autism episodes for most users. One or more of these autism episode alleviation actions can be selected if a particular type of autism episode is detected. In some embodiments, the autism episode alleviation actions could be designated to address specific types of autism episodes for a particular user.

After an autism episode alleviation action is selected, it is presented to the user at 413. In some embodiments, an autism episode alleviation action is automatically presented to the user without any prompts or input from the user. In other embodiments, the user may be presented with a choice of autism episode alleviation actions. For instance, a user may be presented with a choice between a story and a song. The user can then make a selection using a button or other input device on the band. In the present embodiment, the autism episode alleviation action can be provided through an output interface (e.g. display or screen) and/or speakers. Additionally, vibrations can be used in some examples as part of an autism episode alleviation action.

Figure 5:
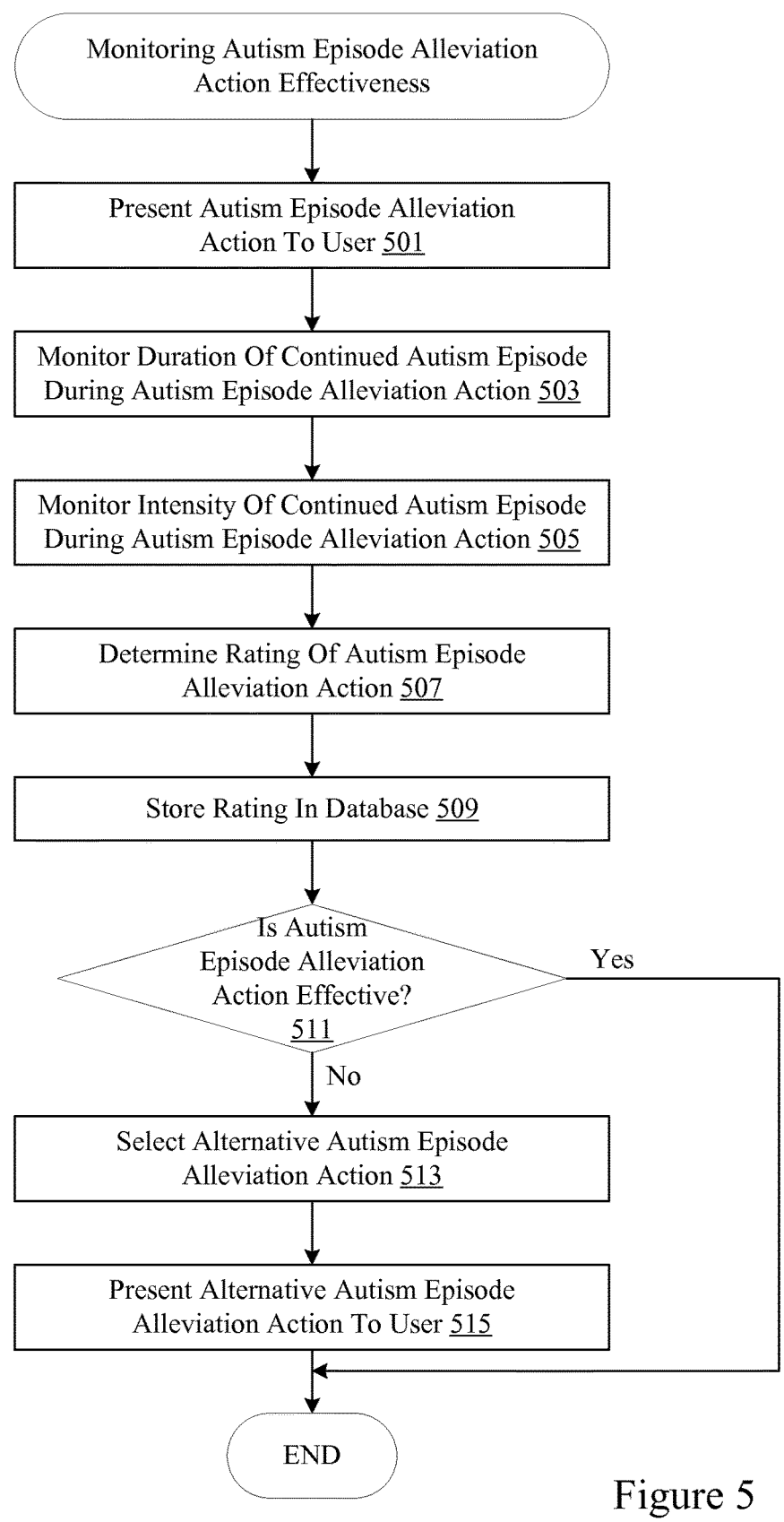
FIG. 5 illustrates an example of monitoring the effectiveness of an autism episode alleviation action.

FIG. 5 illustrates one example of monitoring the effectiveness of an autism episode alleviation action. By monitoring the effectiveness of a particular autism episode alleviation action, the user and any therapists, doctors, family members, etc. can become aware of which treatments are most effective for the user. Furthermore, data about the effectiveness of particular autism episode alleviation actions provided in response to certain autism episodes can be used to select the most effective autism episode alleviation actions for future autism episodes. In some embodiments, this can be used to constantly refine which autism episode alleviation actions are selected for a user, thus providing a dynamic treatment system that can change along with the user.

In the present exemplary embodiment, an autism episode alleviation action is presented to a user at 501. As described in more detail above with regard to FIGS. 3 and 4, an autism episode alleviation action can be selected and presented to a user once an autism episode is detected. Next, the duration of the autism episode can be monitored at 503. In the present embodiment, the duration can be measured from the time the autism episode alleviation action is presented. In some embodiments, the duration measurement can be stored in a database. At 505, the intensity of the autism episode can be monitored. In the present embodiment, the intensity can be measured from the time the autism episode alleviation is presented. In some embodiments, the intensity measurement can be stored in a database. In some examples, ongoing intensity measurements can be stored as a table or graph. In other examples, only the highest and/or lowest intensity measurements can be stored.

Based on the duration and/or intensity of the autism episode detected, a rating can be assigned to the autism episode alleviation action at 507. This rating can reflect the effectiveness of the autism episode alleviation action. For instance, a rating of 10 could be assigned to the most effective response to an autism episode alleviation action, and a rating of 1 could be assigned to the least effective response to an autism episode alleviation action. More specifically, a rating of 10 could be assigned when the duration is very short and the intensity is very low. Furthermore, a rating of 1 could be assigned when the duration is long or ongoing and the intensity is very high. At 509, the rating can be stored in a database. In some embodiments the database can store ratings associated with a particular autism episode alleviation action each time the autism episode alleviation action is used. The aggregate of this information can indicate the general effectiveness of the particular autism episode alleviation action. In other embodiments, the database can store ratings categorized by what type of autism episode was detected. The aggregate of this information can indicate the effectiveness of a particular autism episode alleviation action for individual types of autism episodes.

According to the present exemplary embodiment, the rating assigned to the autism episode alleviation action is then used to make a determination about whether the autism episode alleviation action is effective at 511. For instance, a rating from 8 to 10 can indicate that the autism episode alleviation action is effective and a rating from 1 to 7 can indicate that the autism episode alleviation action is not effective. In other examples, a rating from 8 to 10 can indicate that the autism episode alleviation action is effective, a rating from 5 to 7 can indicate that the autism episode alleviation action is moderately effective, and a rating from 1 to 4 can indicate that the autism episode alleviation action is not effective. It should be noted that the ranges described above are examples, and these ranges can be set in various configurations. In some embodiments, a user can determine the ranges. In other embodiments the ranges can be preset.

In the present embodiment, if a determination is made that the autism episode alleviation action is effective, then no further action is taken. However, if a determination is made that the autism episode alleviation action is not effective, then an alternative autism episode alleviation action can be selected at 513. For instance, a new game, song, video, etc. can be selected. In other examples, the alternative autism episode alleviation action can include contacting a parent, relative, caregiver, or the like. After the alternative autism episode alleviation action is selected, it can be presented to the user at 515. In some embodiments, the alternative autism episode alleviation action is automatically presented to the user without any prompts or input from the user. In other embodiments, the user may be presented with a choice of alternative autism episode alleviation actions. For instance, a user may be presented with a choice between a story and a song. The user can then provide a selection using a button or other input device on the band. In the present embodiment, the alternative autism episode alleviation action can be provided through an output interface (e.g. display or screen) and/or speakers. Additionally, vibrations can be used in some examples as part of the alternative autism episode alleviation action.

Once the alternative autism episode alleviation action is presented to the user, the effectiveness of this alternative autism episode alleviation action can be monitored in some embodiments. This type of monitoring can continue for any autism episode alleviation action or alternative autism episode alleviation action presented. In addition, data regarding the effectiveness of various autism episode alleviation actions can be stored in a database in various embodiments. In some examples, this data can be used to improve the selection of which autism episode alleviation action is made for a user once an autism episode is detected. In other examples, this data can be displayed in the form of graphs, tables, statistics, etc. to the user. This type of display can provide valuable information to the user, family members, doctors, therapists, etc. This information can help these individuals better understand the frequency and severity of autism episodes associated with the user, as well as what types of autism episode alleviation actions appear to be beneficial for reducing autism episodes.

While the invention has been particularly shown and described with reference to specific embodiments thereof, it will be understood by those skilled in the art that changes in the form and details of the disclosed embodiments may be made without departing from the spirit or scope of the invention. It is therefore intended that the invention be interpreted to include all variations and equivalents that fall within the true spirit and scope of the present invention.

What is claimed is:

1. A dynamic autism treatment system comprising:
   a plurality of sensors configured to monitor head rolling exhibited by a user on an autism spectrum;
   a processor connected to the plurality of sensors, the processor configured to determine whether the head rolling exhibited by the user is comparable to characteristic repetitive motions data for a type of autism to determine that the user is experiencing an autism episode, the processor being further configured to determine a type of autism episode based on characteristics of the head rolling, the processor further configured to filter out artifacts not related to autism spectrum disorder (ASD) from data detected by the plurality of sensors;
   memory configured to store ASD characteristic repetitive motions data and a plurality of autism episode alleviation actions associated with different types of autism episodes, wherein an autism episode alleviation action is accessed by the processor upon determining that the user is experiencing an autism episode and the type of autism episode, wherein selecting an autism episode alleviation actions includes utilizing prior effectiveness data of specific autism episode alleviation actions used for specific types of autism episodes, thereby continuously refining which autism episode alleviation actions are selected; and
   an output interface physically configured and positioned to display a video to the user in a manner that disrupts repetitive head rolling by the user, the materials being from the autism episode alleviation action, wherein playback of the autism episode alleviation action is triggered when an autism episode threshold is reached, the autism episode alleviation action configured to reduce the severity or duration of the head rolling, and wherein the autism alleviation action is selected based on the type of autism episode detected.

2. The system of claim 1, wherein the system is a bracelet.

3. The system of claim 1, wherein the repetitive motion comprises hand flapping.

4. The system of claim 1, wherein the repetitive motion comprises rocking back and forth.

5. The system of claim 1, wherein the plurality of sensors comprise a gyroscope and an accelerometer.

6. The system of claim 1, wherein the plurality of sensors comprise a rotation and orientation sensor.

7. The system of claim 1, wherein the autism episode alleviation action comprises playing a customized audio clip.

8. The system of claim 1, wherein the autism episode alleviation action comprises providing the user with access to a game.

9. The system of claim 1, wherein the effectiveness of the autism episode alleviation action is monitored by the system.

10. A dynamic autism treatment apparatus comprising:
    a bracelet including a plurality of sensors configured to monitor head rolling exhibited by a user on an autism spectrum; and
    a mobile device comprising:
        a processor connected to the plurality of sensors, the processor configured to determine whether head rolling by the user is comparable to characteristic repetitive motions data for a type of autism to determine that the user is experiencing an autism episode, the processor being further configured to determine a type of autism episode based on characteristics of the head rolling, the processor further configured to filter out artifacts not related to autism spectrum disorder (ASD) from data detected by the plurality of sensors;
        memory configured to store ASD characteristic repetitive motions data and a plurality of autism episode alleviation actions associated with different types of autism episodes, wherein an autism episode alleviation action is accessed by the processor upon determining that the user is experiencing an autism episode and the type of autism episode, wherein selecting an autism episode alleviation action includes utilizing prior effectiveness data of specific autism episode alleviation actions used for specific types of autism episodes, thereby continuously refining which autism episode alleviation action is selected; and
        an output interface physically configured and positioned to display a video to the user in a manner that disrupts repetitive head rolling by the user, the materials being from the autism episode alleviation action, wherein playback of the autism episode alleviation action is triggered when an autism episode threshold is reached, the autism episode alleviation action configured to reduce the severity or duration of the head rolling, and wherein the autism alleviation action is selected based on the type of autism episode detected.

11. The apparatus of claim 10, wherein the bracelet is a watch.

12. The apparatus of claim 10, wherein the repetitive motion comprises hand flapping.

13. The apparatus of claim 10, wherein the repetitive motion comprises rocking back and forth.

14. The apparatus of claim 10, wherein the plurality of sensors comprise a gyroscope and an accelerometer.

15. The apparatus of claim 10, wherein the plurality of sensors comprise a rotation and orientation sensor.

16. The apparatus of claim 10, wherein the autism episode alleviation action comprises playing a customized audio clip.

17. The apparatus of claim 10, wherein the autism episode alleviation action comprises providing the user with access to a game.

18. The apparatus of claim 10, wherein the effectiveness of the autism episode alleviation action is monitored by the system.

\* \* \* \* \*